US011986568B2

(12) United States Patent
Pema

(10) Patent No.: US 11,986,568 B2
(45) Date of Patent: May 21, 2024

(54) METHOD FOR THE REDUCTION OF FIXATION PIN TRACK INFECTIONS

(71) Applicant: Prevent-Plus, LLC, St. Louis, MO (US)

(72) Inventor: Shital Pema, Dayton, OH (US)

(73) Assignee: PREVENT-PLUS, LLC, St. Louis, MO (US)

( * ) Notice: Subject to any disclaimer, the term of this patent is extended or adjusted under 35 U.S.C. 154(b) by 496 days.

(21) Appl. No.: 16/594,452

(22) Filed: Oct. 7, 2019

(65) Prior Publication Data

US 2020/0114028 A1 Apr. 16, 2020

Related U.S. Application Data

(60) Provisional application No. 62/741,627, filed on Oct. 5, 2018.

(51) Int. Cl.
*A61L 2/18* (2006.01)
*C08L 69/00* (2006.01)
*A61B 17/62* (2006.01)

(52) U.S. Cl.
CPC ............... *A61L 2/18* (2013.01); *C08L 69/00* (2013.01); *A61B 17/62* (2013.01); *A61L 2202/20* (2013.01)

(58) Field of Classification Search
CPC ........ A61L 2/18; A61L 2202/20; C08L 69/00; A61B 17/62; A61B 17/60; A61B 17/6425; C08G 64/0208
See application file for complete search history.

(56) References Cited

U.S. PATENT DOCUMENTS

| 4,856,504 | A | * | 8/1989 | Yamamoto | ........ A61F 13/49009 606/59 |
| 4,961,417 | A | * | 10/1990 | Young | ..................... A61B 17/60 602/6 |
| 6,909,027 | B1 | | 6/2005 | Robins et al. | |
| 7,119,246 | B2 | | 10/2006 | Robins et al. | |
| 9,867,891 | B2 | * | 1/2018 | Russell | ................... B32B 5/022 |
| 2009/0036645 | A1 | * | 2/2009 | Stopek | .................... A61L 27/34 528/425 |
| 2014/0350017 | A1 | * | 11/2014 | Williams | .............. C07C 217/54 514/237.8 |

OTHER PUBLICATIONS

Sherry H. Hsiung & Perry Robbins, Evaluation of a Flexible New Liquid Polymer Wound Dressing, Journal of Drugs in Dermatology, Sep./Oct. 2005, pp. 2-4, vol. 4, Issue 5, New York University.
Perry Robins et al., The Effectiveness of Liquid Bandage as an Adhesive and Antimicrobial Agent, Journal of Drugs in Dermatology, Aug. 2008, pp. 2-5, vol. 7, Issue 8.
Shital Pema, Retrospective Evaluation of Microbicidal Polymer Dressing for Reduction of Infection Following Post Deformity Correction Surgery, J Drugs Dermatol. 2018;17(12);1322-1324.

\* cited by examiner

*Primary Examiner* — Regina M Yoo
(74) *Attorney, Agent, or Firm* — Welsh Flaxman & Gitler LLC

(57) ABSTRACT

A method for reducing fixation pin track infection rates after the formation of at least one fixation pin track by penetrating skin of patient with a fixation pin as the fixation pin is anchored within an adjacent bone includes applying a composition to a pin site in an area surrounding the fixation pin track, and allowing the composition to form a film covering the pin site.

7 Claims, 1 Drawing Sheet

METHOD FOR THE REDUCTION OF FIXATION PIN TRACK INFECTIONS

CROSS REFERENCE TO RELATED APPLICATION

This application claims the benefit of U.S. Patent Application Publication No. 62/741,627, entitled "METHOD FOR THE REDUCTION OF FIXATION PIN TRACK INFECTIONS," filed Oct. 5, 2018.

BACKGROUND OF THE INVENTION

1. Field of the Invention

The present invention relates to a method for the reduction of fixation pin track infections in patients subjected to external fixation.

2. Description of the Related Art

Metal pins are commonly used for external fixation in patients undergoing reconstructive or repair surgery. These pins protrude through the skin and create an avenue for the migration of organisms. Anytime there is a break in the integrity of the skin, the risk of infection is increased. Pin site infections are a very common complication of external fixation, and unfortunately, the literature is scant on how to optimally minimize the risk of infection.

A Cochrane Collaboration Review published in 2004 assessed the effect on infection rates of different methods of cleaning and dressing orthopedic percutaneous pin sites and determined that there was little evidence as to which pin site care regimen best reduces infection rates. Temple J, Santy J. Pin site care for preventing infections associated with external bone fixators and pins. Cochrane Database of Systematic Reviews 2004, Issue 1. Art. No.:CD004551. DOI: 10.1002/14651858.CD004551.

Depending on the reference, pin track infections rates have been reported to range from 0% to 100%. A systematic view of the incidence of pin track infections associated with external fixation published in 2016 revealed a cumulative pin track infection rate of 27%. This rate was defined as the inherent risk of any given patient developing a pin track infection at a random pin or wire site during the course of treatment with external fixation. Iobst CA, Liu RW. A systematic review of incidence of pin track infections associated with external fixation. J Limb Lengthen Reconstr 2016; 2:6-16. A 2016 review describes pin track infection as the most commonly expected problem, or even an almost inevitable complication, when using external fixation. Ceroni D, et al. From Prevention of pin-tract infection to treatment of osteomyelitis during paediatric external fixation. J Child Orthop 2016; 10:605-612.

SUMMARY OF THE INVENTION

It is, therefore, an object of the present invention to provide a method for reducing fixation pin track infection rates after the formation of at least one fixation pin track by penetrating skin of patient with a fixation pin as the fixation pin is anchored within an adjacent bone. The method comprises applying a composition to a pin site in an area surrounding the fixation pin track and allowing the composition to form a film covering the pin site.

It is also an object of the present invention to provide a method wherein the composition is a polyalkylene carbonate composition.

It is another object of the present invention to provide a method wherein the polyalkylene carbonate composition consists of polyalkylene carbonate polymer dissolved in methylene chloride organic solvent.

It is a further object of the present invention to provide a method wherein the polyalkylene carbonate composition consists of 7.5%-10% by weight polyalkylene carbonate polymer dissolved in 90%-92.5% by weight methylene chloride organic solvent.

It is also an object of the present invention to provide a method removing the film thereby carrying with the film dirt, oil, dead skin cells and bacteria incorporated into the film.

It is another object of the present invention to provide a method wherein the area surrounding the fixation pin track extends at least one inch beyond an edge of the pin site surrounding the fixation pin track.

It is further an object of the present invention to provide a method wherein a thickness of the film is 0.25 mils to 3.5 mils.

It is also an object of the present invention to provide a method further including brushing of the pin site with saline to remove debris prior to the step of applying the composition to the pin site.

It is another object of the present invention to provide a method wherein the steps of brushing, applying and allowing are repeated.

It is a further object of the present invention to provide a method wherein the step of applying includes applying the composition with a cotton swab applicator.

It is also an object of the present invention to provide a method further including the step of applying the composition on the fixation pin.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
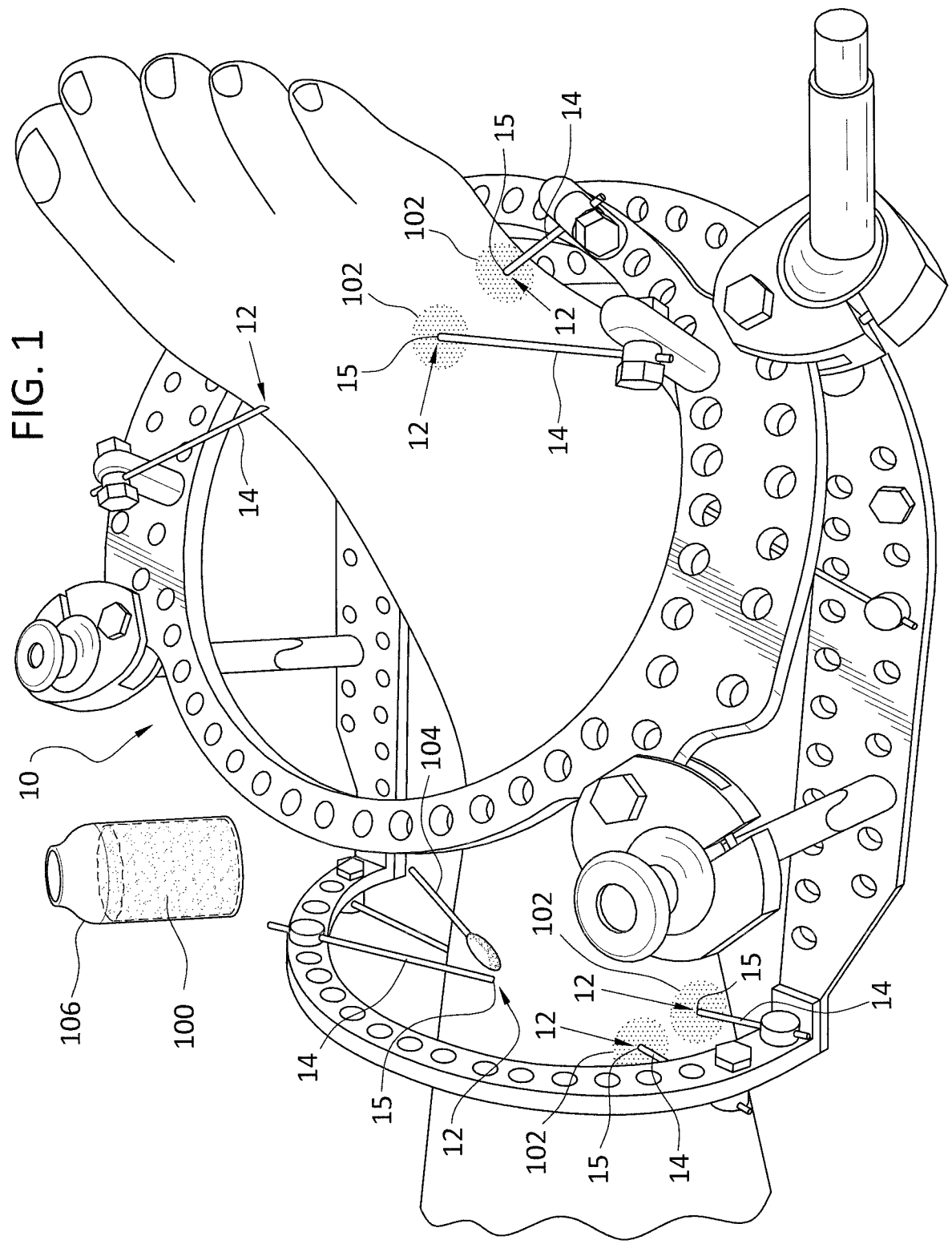
FIG. 1 is a perspective view of a patient being treated in accordance with the present method.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to FIG. 1 and the following disclosure, the present invention provides a method for reducing fixation pin track infection rates associated with treatment by an external fixation apparatus 10 following deformity correction and traumatic provisional fixation. In accordance with a preferred embodiment, and as will be explained below in greater detail, topically applied polyalkylene carbonate polymer in a fluid form, that is, as a liquid, ("polyalkylene carbonate composition") 100 is employed as an additional step in the treatment protocol for pin site care. As those skilled in the art will appreciate, "pin site" 12 is meant to refer to the location where a fixation pin 14 penetrates the skin of a patient as it is anchored within the adjacent bone. Initial research on approximately 25 research patients with a total of over 200 pin sites resulted in only 2 pin site infections. This represents a significant reduction from the average incidence of pin site infections reported in the literature (<1% vs 27% on a per research patient basis).

The polyalkylene carbonate composition 100 applied to the pin sites 12 is that disclosed in U.S. Pat. No. 6,909,027, entitled METHOD OF FORMING AN IN-SITU FILM DRESSING AND THE COMPOSITION OF THE FILM-FORMING MATERIAL and U.S. Pat. No. 7,119,246, entitled METHOD OF TREATING ACNE, both of which are incorporated herein by reference. As these patents explain, the polyalkylene carbonate polymers can be employed in the form of an emulsion, a suspension, or a solution of the polyalkylene carbonate polymer in a biocompatible medium. In all instances the polyalkylene carbonate composition 100, in particular, the polyalkylene carbonate polymer, forms a film 102 upon application to cover the pin site 12 to be treated. As the polyalkylene carbonate composition 100 flows across the pin site 12 to be treated it penetrates the pores in the pin site 12, and any dirt, dead skin cells and bacteria are incorporated into the film 102 formed as the polyalkylene carbonate composition 100 dries (that is, polyalkylene carbonate film). Not only does the film 102 form a barrier to external dirt, bacteria and skin cells, but any dirt, dead skin cells and bacteria found already existing in the pin site 12 are incorporated into the polyalkylene carbonate film 102. When the fluid polyalkylene carbonate film 102 is thereafter removed from the pin site 12 to be treated, it carries with it the dirt, oil, dead skin cells and bacteria incorporated into the polyalkylene carbonate film 102.

In accordance with a preferred embodiment, the polyalkylene carbonate composition 100 is DuraDerm®, a 510K FDA cleared medical device indicated for providing a covering over minor wounds and scrapes that are clean and dry. DuraDerm® consists solely of organic polyalkylene carbonate polymer (7.5%-10% by weight) dissolved in methylene chloride organic solvent (90%-92.5% by weight). The formulation eradicates any organisms (bacteria, fungi, viruses) it comes in contact with. This is a result of the methylene chloride's activity against an infinite number of organisms. The methylene chloride evaporates leaving a clear, elastomeric, non-odorous polyalkylene carbonate film 102 covering the area surrounding the fixation pin tracks 15 (that is, the location where the fixation pin 14 penetrates the skin). As used herein, the term "pin site" is use to refer to the area surrounding pin track. The polyalkylene carbonate film 102 protects against entry of water, dirt, and germs. The polyalkylene carbonate film 102 formed after application in accordance with the present invention is elastomeric and protects in difficult regions where flexing, bending and creasing skin occurs. The clear polyalkylene carbonate film 102 forms in less than one minute. Application is commonly accomplished using a cotton tip applicator 104. The polyalkylene carbonate composition 100 is applied on and around the pin site 12 surrounding each of the fixation pin tracks 15 such that the polyalkylene carbonate composition 100 extends at least an inch beyond the edges of the pin site 12 surrounding each of the fixation pin tracks 15 (that is, radially extending at least an inch from the place at which the fixation pin 14 penetrates the skin). Momentary stinging may occur upon initial application. The polyalkylene carbonate film 102 commonly remains intact for one to three days or longer depending on exposure to rubbing, flexing, or soap and water. This polyalkylene carbonate film 102 is resistant to degradation by water alone, but can be easily removed with the combination of soap and water or it can be gently peeled off starting at the outer edges.

The polymers called polyalkylene carbonates are utilized to provide an optimum environment and mechanism in and around the pin site 12 surrounding each of the fixation pin tracks 15. These polymers are produced by reacting carbon dioxide with epoxides. Inoue S, "Organic and Bio-Organic Chemistry of Carbon Dioxide" Halsted Press, New York, pp 167-176, 1982. The resulting properties of the polymer are a function of the epoxide selected.

Polyalkylene carbonate polymers can be produced with properties that range from soft elastomeric with low glass transition temperatures (15° C. to 25° C. to 40° C.), to hard stiff polymers with high glass transition temperatures, e.g. 132° C. Intermediate properties can be produced by chemical (terpolymers) and physical (blends) means.

Films made from these polymers adhere to skin forming a barrier to outside dirt, water, and bacteria, penetrate the pin site 12 being treated and result in any dirt, oil, dead skin cells and bacteria in the treated pin site 12 being incorporated into the film. Upon removal from the treatment site, and as discussed above, the polyalkylene carbonate film 102 also removes the materials incorporated into it.

Polyalkylene carbonate films 102 will not adhere to any open sores or wounds in the treated pin site 12, thereby permitting frequent dressing changes without disturbing the normal healing process of the affected pin site 12. Additionally, polyalkylene carbonate polymers can be dissolved in a number of biologically acceptable solvents. As such, and further to the preferred polyalkylene carbonate composition described above, it is appreciated the polyalkylene carbonate composition may be composed of one or more polyalkylene carbonates with one or more solvents to resulting in a desired fluid, including foams or gels. It is also appreciated, polyalkylene carbonate polymers can also be produced as water based emulsions.

Physical and chemical properties of one or more of this family of polyalkylene carbonate polymers which can be selectively utilized are:
   clear, amorphous, thermoplastic;
   glass transition temperatures in the range of from about 15° C. to about 132° C.;
   excellent adhesion to skin, non-sticking to wound;
   soft, elastomeric polymers with good recovery, to hard engineering polymers;
   low cost;
   quick drying with no odor;
   soluble in a wide range of solvents from low boiling to high boiling;
   low glass transition temperature of polyethylene carbonates, e.g. 20° C. to 25° C.;
   makes for a soft, flexible and elastic film, which is softened by the skin and body temperature causing flow of the polyalkylene carbonate and promoting conformability to body shapes in motion;
   barrier to outside water, dirt, and bacteria; and
   can be produced as water based emulsions.

As mentioned above, the polyalkylene carbonate polymers used in accordance with the present invention are dissolved in a biocompatible solvent or solvents, in particular, methylene chloride. Other solvents that can be used include dichloroethane, propylene carbonate, dimethylformamide, N-Methyl pyrrolidone, acetone, ethyl acetate, tetrahydrofuran, methyl ethyl ketone as well as other ketones, esters, ethers, etc. The polymer concentration in the fluid is ultimately a function of the delivery system selected.

In accordance with one embodiment, the polyalkylene carbonate composition 100 is as follows: a base solution of polyethylene carbonate having a glass transition temperature (Tg) of about 22° C. is dissolved in methylene chloride to provide a solution in which the polyethylene carbonate is present in a concentration of 7.5%-10% by weight based upon the solution. The polyalkylene carbonate composition 100 should be stored in a glass container 106, as it is known that methylene chloride reacts with plastics.

The use of polyethylene carbonate as the polyalkylene carbonate polymer in accordance with the present invention results in a polyalkylene carbonate composition 100 with excellent oxygen barrier properties, low Tg of about 22° C., very high elongation and recovery, flexibility and elasticity provides excellent conformity and protection to irregular body shapes. The low Tg, permits body skin temperatures to soften the polymer further and better conform to irregular shapes, increasing the patient's comfort and providing excellent protection to the treatment area. Film thickness can be from about 0.25 mils (0.25 thousandth of an inch) to greater than about 3.0 mils (3.0 thousandth of an inch), e.g., about 3.5 mils (3.5 thousandth of an inch).

In certain cases, external oxygen may be desired and, therefore, polypropylene carbonate can be used, since it is not a good oxygen barrier. For example, and in accordance with another embodiment, a base solution of polypropylene carbonate having a glass transition temperature (Tg) of 40° C. is dissolved in methylene chloride to provide a solution in which the polyethylene carbonate is present in a concentration of 15% by weight based upon the solution.

By blending polyalkylene carbonate polymers, e.g., polypropylene carbonate and polyethylene carbonate, either physically or chemically (terpolymer), intermediate properties can be obtained to optimize treatment.

There are no other polymer families that can incorporate the unique broad range combination of physical/chemical properties obtainable with this recently developed family of polymers, polyalkylene carbonates. They can be "tailored" to fit the application, thereby providing a better healing system, reducing scarring which adds to patient comfort, and reducing costs.

In practicing the method of the present invention, it is desired that the polyalkylene carbonate film 102 covering the pin site 12 surrounding each of the fixation pin tracks 15 is to be maintained on the treated area until the following day when the pin site 12 is once again subjected to daily brushing.

While a variety of alkylene substituents can be employed in the polyalkylene carbonate polymer of the present invention to alter the properties of the final polymer or polymers, it is preferred to utilize polymers having lower alkylene substituents containing less than about 12 carbon atoms and particularly less than about 10 carbon atoms. Typically, polyalkylene carbonate carbonates having from about 2 up to about 9 carbon atoms are employed. Most frequently, ethylene, propylene or butene are used as the alkylene substituent in the polyalkylene carbonate polymers of the present invention.

In accordance with the present invention the method for a reduction in pin track infection is achieved in the following manner.

While the patients are hospitalized, all fixation pin (and/or wire) sites 12 are cleaned daily. Fixation pin care is performed once daily by hospital nursing staff prior to discharge.

In particular, the following protocol is followed while the patient is hospitalized:
Step 1: Daily brushing the pin sites 12, with saline using an ordinary soft toothbrush or gauze with sterile gloves (so as to prevent skin from attaching to the fixation pins, decrease the chance of infection, and inspect the area for any signs of infection).
Step 2: If following Step 1, debris remains, using forceps (tweezers) to gently remove debris.
Step 3: Daily applying the polyalkylene carbonate composition 100 with a brush, for example, a Q-Tip® cotton tip applicator 104, on clean dry wound around (extending at least one inch around the pin site 12, and preferably at least 1¼ inches around the pin site 12) and on the fixation pin 14.

Following discharge from the hospital, the fixation pin care protocol is continued by the patient's caregiver as follows:
Step 1: Daily brushing the pin sites 12, with saline using an ordinary soft toothbrush or gauze with sterile gloves.
Step 2: If following Step 1, debris remains, using forceps (tweezers) to gently remove debris.
Step 3: Minimally at least three times a week applying polyalkylene carbonate composition 100 with a Q-tip® cotton tip applicator 104 on clean dry wound around (extending approximately one inch around pin site 12) and on the fixation pin 14.

Ideally, pin sites 12 are cleaned when the surrounding skin and gauze are soft. This makes removal of gauze and cleaning of fixation pins 14 less painful. The purpose of the cleaning is to prevent the skin from attaching to the fixation pins 14 (and wires) and to decreases the chance of infection, as well as, to inspect the pin site 12 for any signs of infection. In accordance with an embodiment of the present method, the fixation pin care protocol is continued by the patient's caregiver on average three times a week for 5-8 weeks after discharge from the hospital until the fixation pins 14 are removed. After the pins are removed, the care protocol, with the exception of applying the polyalkylene carbonate composition on the fixation pins 14, is continued for approximately 14 days.

As to Step 3, and whether in the hospital or at home, prior to the application of the polyalkylene carbonate composition 100, the pin site 12 surrounding each of the fixation pin tracks 15 is dried. The pin site 12 is then coated with the polyalkylene carbonate composition 100 and allowed to dry. The drying process is a matter of minutes due to the low boiling point of the solvent, i.e. 39.7° C. The skin temperature is about 33° C., body temperature about 37° C., promoting evaporation of the solvent, and flow of the polyalkylene carbonate polymer, which has a glass transition temperature of about 20-25° C., thereby resulting in the flow of polyalkylene carbonate into the pores in the pin site 12.

Since a Q-tip® cotton tip applicator 104 application is being used, a polyalkylene carbonate composition 100 with an intermediate polyalkylene carbonate polymer concentration is used with proper viscosity to prevent the polyalkylene carbonate composition from running away from the pin site 12 to be treated. Polyalkylene carbonate polymer concentrations in this application are usually range of from about 7.5% to about 10% by weight of the solution. This would also apply with an eye-dropper or rod application.

While a brush type application, through the use of a cotton swab applicator 104, is described above, it is appreciated other modes of application, for example, bristle-type (or similar) brushes, spraying, gel or squeeze tube application, or emulsion application may be used.

Testing of the above methodology was performed and the results are found in Perna, S.; *Retrospective Evaluation of Microbicidal Polymer Dressing for Reduction of Infection Following Post Deformity Correction Surgery*, J Drugs Dermatol. 2018 Dec. 1; 17(12):1322-1324, which is incorporated herein by reference. The evaluation found the no patients (totally 6 patients with a total of 66 pins) developed clinical signs of pin track infection according to the a Classification of Pin Track Infection wherein Grade 1 is defined as irritation of pin surrounding area by adhesions and restriction of movement; Grade 2 is defined as infection of the pin surrounding area without secretion; and Grade 3 is defined as a Grade 2 infection but with definite pin track secretion, without significant pin loosening.

Further testing has demonstrated similar results. For example, testing of 13 patients (7 treated in accordance with the present invention and 6 non-treated) resulted in a zero infections rate for the treated patients and 33% infection rate for the non-treated patients.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for reducing fixation pin track infection rates after the formation of at least one fixation pin track by penetrating skin of patient with a fixation pin as the fixation pin is anchored within an adjacent bone, comprising:
    brushing a pin site with saline to remove debris prior to application of a polyalkylene carbonate composition to the pin site, so as to prevent skin from attaching to the fixation pins, decrease chance of infection, and inspect area for any signs of infection;
    applying the polyalkylene carbonate composition to a clean dry wound around the pin site in an area surrounding the fixation pin track such that the polyalkylene carbonate composition extends at least an inch beyond edges of the pin site surrounding each fixation pin track;
    allowing the polyalkylene carbonate composition to form a film covering the pin site, wherein any dirt, dead skin cells and bacteria found already existing in the pin site are incorporated into the film and subsequent removal of the film carries away the film dirt, oil, dead skin cells and bacteria incorporated into the film; and
    repeating the steps of brushing, applying, and allowing, wherein the film covering the pin site is maintained until the pin site is once again subjected to brushing as a result of repeating.

2. The method according to claim 1, wherein the polyalkylene carbonate composition consists of polyalkylene carbonate polymer dissolved in methylene chloride organic solvent.

3. The method according to claim 2, wherein the polyalkylene carbonate composition consists of 7.5%-10% by weight polyalkylene carbonate polymer dissolved in 90%-92.5% by weight methylene chloride organic solvent.

4. The method according to claim 1, wherein a thickness of the film is 0.25 mils to 3.5 mils.

5. The method according to claim 1, wherein the step of applying includes applying the polyalkylene carbonate composition with a cotton swab applicator.

6. The method according to claim 1, further including a step of applying the polyalkylene carbonate composition on the fixation pin.

7. The method according to claim 1, wherein the step of repeating the steps brushing, applying, and allowing is performed on a daily basis.

* * * * *